US012594112B2

(12) United States Patent
    Goulko et al.

(10) Patent No.: US 12,594,112 B2
(45) Date of Patent: Apr. 7, 2026

(54) CRYOGENIC APPLICATOR

(71) Applicant: Cryogeneus Inc., Fort Lee, NJ (US)

(72) Inventors: Olga Goulko, Cliffside Park, NJ (US);
                Khasanbi Erganokov, Moscow (RU);
                Valentin Pavlov, Moscow (RU)

(73) Assignee: Cryogeneus Inc., Fort Lee, NJ (US)

( * ) Notice: Subject to any disclaimer, the term of this
              patent is extended or adjusted under 35
              U.S.C. 154(b) by 910 days.

(21) Appl. No.: 17/282,800

(22) PCT Filed: Oct. 7, 2019

(86) PCT No.: PCT/US2019/054947
     § 371 (c)(1),
     (2) Date: Apr. 5, 2021

(87) PCT Pub. No.: WO2020/076675
     PCT Pub. Date: Apr. 16, 2020

(65) Prior Publication Data
     US 2021/0378727 A1      Dec. 9, 2021

Related U.S. Application Data

(60) Provisional application No. 62/742,513, filed on Oct.
     8, 2018.

(51) Int. Cl.
     *A61B 18/02*       (2006.01)
     *A61B 18/00*       (2006.01)

(52) U.S. Cl.
     CPC .................... *A61B 18/0218* (2013.01); *A61B
           2018/00136* (2013.01); *A61B 2018/00148*
                                              (2013.01);
                         (Continued)

(58) Field of Classification Search
     CPC ............ A61B 18/02; A61B 2018/0262; A61B
                            18/0218; A61B 2018/00041;
                         (Continued)

(56) References Cited

U.S. PATENT DOCUMENTS 3,333,587 A      8/1967  Johnston
3,736,936 A *    6/1973  Basiulis ................. A61B 18/02
                                                   607/105

(Continued)

FOREIGN PATENT DOCUMENTS

KR     2020090000258 U    1/2009
WO        2007081400 A1   7/2007
WO        2018142411 A1   8/2018

OTHER PUBLICATIONS

Extended European Search Report, EP Application 19870307.6, Jul.
2022.
English Abstract for KR2020090000258 U, Jan. 9, 2009.

*Primary Examiner* — Linda C Dvorak
*Assistant Examiner* — Lindsay Regan Lancaster
(74) *Attorney, Agent, or Firm* — CAHN & SAMUELS,
LLP; George Metzenthin

(57)                     ABSTRACT

A portable cryogenic applicator includes a vessel for liquid nitrogen to deliver liquid nitrogen for treatment of skin surfaces using the rotating roller from porous biocompatible material. The cryogenic applicator includes a capillary U-bend to prevent spontaneous discharge of liquid nitrogen through the capillary system to the roller during filling or refilling the cryogenic applicator with liquid nitrogen. The cryogenic applicator also includes a vacuum valve that produce an insulating vacuum environment in a vacuum cavity to prevent heat transfer between the vessel for liquid nitrogen and a vacuum casing, which allows the external surface of the cryogenic applicator to be maintained at ambient temperature. The cryogenic applicator may include a control valve for regulating and maintaining the working pressure in the vessel for liquid nitrogen sufficient to deliver liquid nitrogen through the capillary system and the porous roller body to the surface skin of a patient.

19 Claims, 5 Drawing Sheets

(52) U.S. Cl.
CPC ............... *A61B 2018/00452* (2013.01); *A61B 2018/0262* (2013.01)

(58) Field of Classification Search
CPC .. A61B 2018/0212; A61B 2018/00101; A61B 2018/0275; A61B 2017/00084; A61B 2018/00095; A61B 2018/00166; A61B 2018/0293; A61B 2218/002; F17C 2221/014; F17C 2223/0161; F17C 2270/02; F17C 2201/032; F17C 2201/058; F17C 2205/0332; F17C 2205/0382; F17C 2223/047; F17C 2270/0509; F17C 9/00; F17C 2203/0629; F17C 2225/0161; F25D 3/10; F25D 3/107; F04C 2270/0421; A45D 34/04; B65D 83/285
See application file for complete search history.

(56) References Cited

U.S. PATENT DOCUMENTS

| | | | | |
|---|---|---|---|---|
| 3,736,937 A * | 6/1973 | Basiulis | ................. | A61B 18/02 606/116 |
| 4,154,364 A * | 5/1979 | Hagiwara | ............. | C01B 3/0057 220/592.27 |
| 4,201,319 A * | 5/1980 | Andera | .................... | A61D 7/00 222/399 |
| 4,202,336 A * | 5/1980 | van Gerven | ........... | A61B 18/02 606/24 |
| 4,345,598 A | 8/1982 | Zobac et al. | | |
| 4,838,034 A * | 6/1989 | Leonard | .................... | F17C 9/02 62/51.1 |
| 4,854,128 A * | 8/1989 | Zeamer | ..................... | F17C 9/00 62/51.1 |
| 5,086,619 A * | 2/1992 | Huang | .................... | G01J 5/061 62/51.1 |
| 5,382,797 A * | 1/1995 | Kunimoto | ............... | G01J 5/061 250/352 |
| 6,039,730 A * | 3/2000 | Rabin | .................... | A61B 90/17 606/22 |
| 6,077,046 A * | 6/2000 | Kennedy | ................. | F04B 37/02 417/48 |
| 6,430,956 B1 * | 8/2002 | Haas | ....................... | A61B 18/02 62/293 |
| 7,799,018 B2 | 9/2010 | Goulko | | |
| 7,993,330 B2 | 8/2011 | Goulko | | |
| 2003/0100936 A1 * | 5/2003 | Altshuler | ............... | A61H 99/00 607/96 |
| 2004/0204705 A1 * | 10/2004 | Lafontaine | ......... | A61B 18/0218 606/23 |
| 2005/0016186 A1 * | 1/2005 | Tom | .......................... | F17C 5/06 62/48.1 |
| 2007/0161975 A1 * | 7/2007 | Goulko | .............. | A61B 18/0218 606/23 |
| 2008/0183167 A1 * | 7/2008 | Britva | .................. | A61B 18/042 606/41 |
| 2010/0185266 A1 * | 7/2010 | Suzuki | ................. | A61N 5/0624 607/90 |
| 2011/0301585 A1 | 12/2011 | Goulko | | |
| 2012/0209363 A1 * | 8/2012 | Williams, III | ........... | A61F 7/02 607/114 |
| 2013/0197473 A1 * | 8/2013 | McMillan | ................ | A61B 5/01 604/501 |
| 2017/0014174 A1 * | 1/2017 | Levine | ................... | G05B 15/02 |
| 2019/0086120 A1 * | 3/2019 | Zhou | .................... | F16K 17/0473 |

* cited by examiner

1 - vessel for liquid nitrogen
2 - vacuum casing
4 - roller
5a - feeding capillary
5b - forming capillary
5c - thermostatic capillary
6 - evaporation chamber with radial holes
7 - cryo-adsorbent
8 - vacuum cavity
9 - conduit
10 - vacuum and safety valve
11 - U-bend
12a - inlet of the feeding capillary
14 - control and safety valve
15a - back slide bearing
15b - front slide bearing
16 - roller retainer
18 - neck
19 - gasket
20 - hydrogen absorber
21 - filter

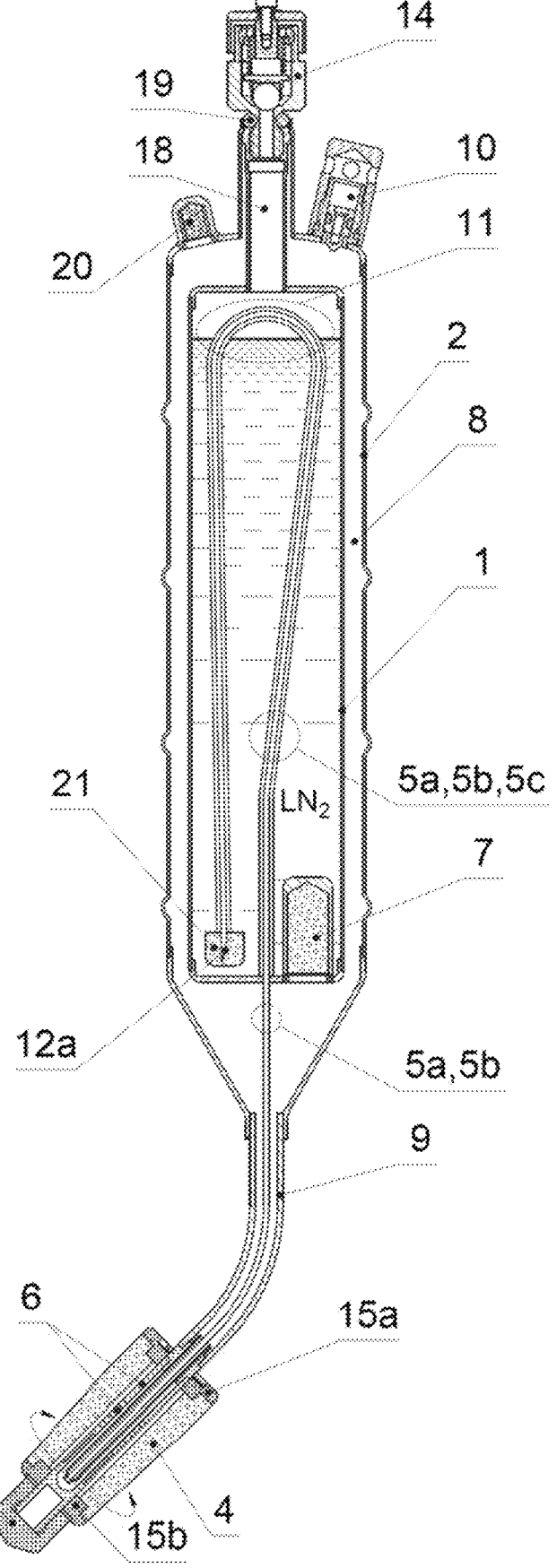

Fig. 1

3 - adapter bushing

4 - roller

6 - evaporation chamber with radial holes

9 - conduit

13a - outlet of the feeding capillary

13b - outlet of the forming capillary

15a - back slide bearing

15b - front slide bearing

16 - roller retainer

17 - stopper ring with washer

3 - adapter bushing

4 - roller

9 - conduit

15a - back slide bearing

15b - front slide bearing

16 - roller retainer

17 - stopper ring with washer

1 - vessel for liquid nitrogen
2 - vacuum casing
5a - feeding capillary
5b - forming capillary
5c - thermostatic capillary
7 - cryo-adsorbent
8 - vacuum cavity
10 - vacuum and safety valve
11 - U-bend
12a - inlet of the feeding capillary
12b - inlet of the forming capillary
20 - hydrogen absorber
21 - filter
22a - metal mesh
22b - metal mesh
23 - level of liquid nitrogen T1 - temperature of liquid nitrogen
T2 - temperature above liquid nitrogen level
T3 - temperature of liquid nitrogen in the forming capillary before U-bend
T4 - temperature of liquid nitrogen in the forming capillary behind U-bend $$T_1 < T_2$$
$$T_1 = T_3 = T_4$$

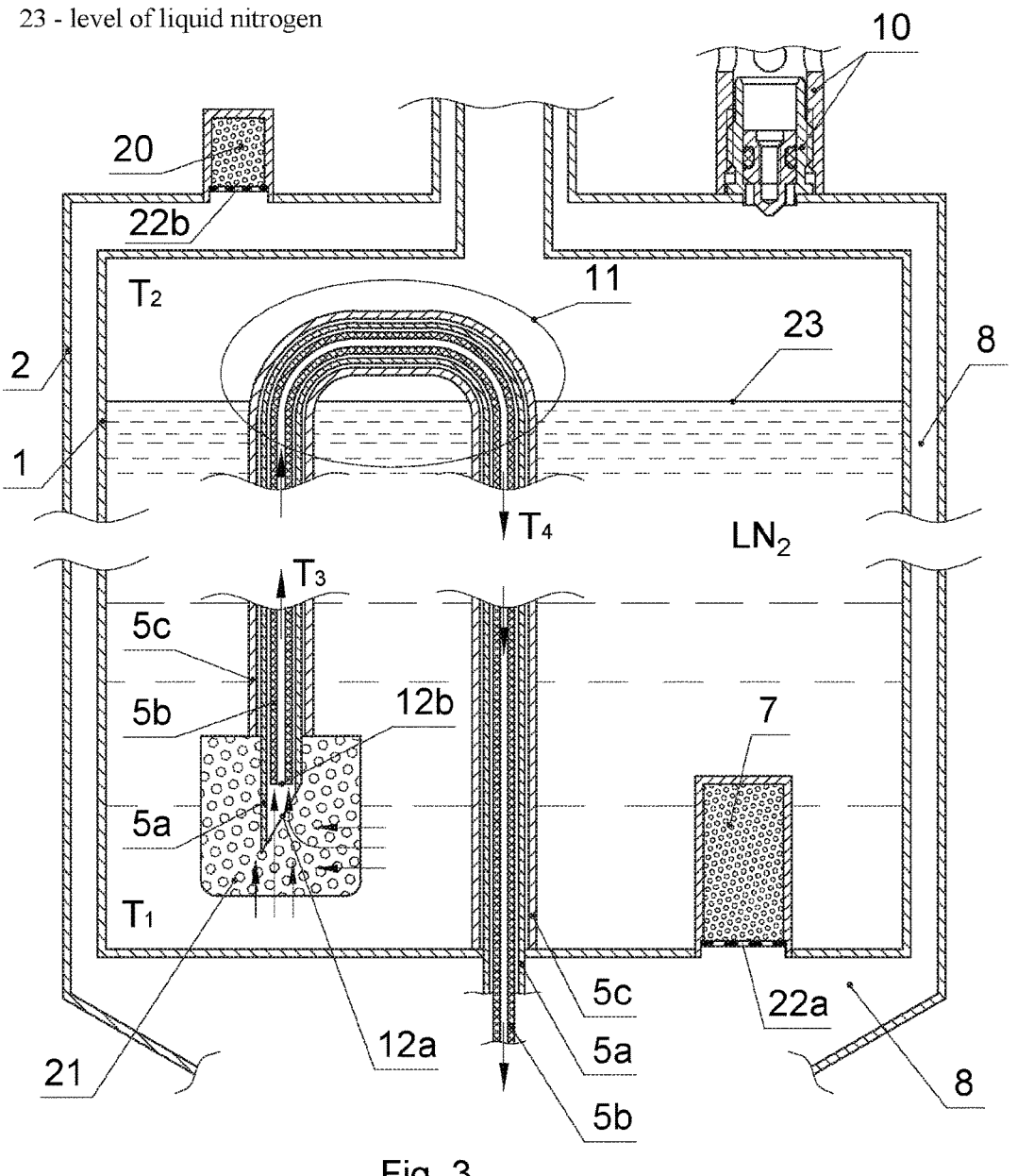

Fig. 3

24 - base

25 - socket

26 - stand

27 - support funnel

CRYOGENIC APPLICATOR

This U.S application is a national stage application of PCT international application PCT/US2019/054947 filed on 10 Oct. 2019 and claims priority to U.S. Ser. No. 62/742, 513, which was filed in the U.S. Patent and Trademark Office on 8 Oct. 2018, the entirety of which is incorporated herein by reference.

I. FIELD OF THE INVENTION

The present invention relates to medical equipment, namely to cryogenic applicators intended to apply a cryogenic fluid, for example liquid nitrogen, to skin surfaces for various medical and cosmetic skin care procedures, and methods of use thereof.

II. BACKGROUND OF THE INVENTION

Liquid nitrogen (and/or other biocompatible non-toxic cryogenic liquids) has been used nearly for the last one hundred years, as described by the American Academy of Family Physicians (e.g. https://www.aafp.org/afp/2004/0515/p2365.html) for treatment of various problems of the skin and other tissues, and this treatment is known as "cryotherapy" or "cryosurgery".

The most frequently cryotherapy is used in dermatology to treat numerous skin problems such as sun damage, skin cancer, keloid scars, acne, various benign skin lesions such as warts, seborrheic keratosis and so on. The boiling temperature of liquid nitrogen is about −321° F. It has been known that use of liquid nitrogen was shown to induce immunological cascade that replaces old cells with new and healthier cells, and this effect is known as apoptosis. This effect is used to treat the skin and can be used to rejuvenate the skin.

Recently, cryotherapy has become a more popular procedure and is used in various areas of medicine, for example, cryolipolysis in aesthetic medicine to reduce adipose tissues, cryoablation in cardiology to restore the damaged cardiac muscle, cryosauna in rheumatology to reduce inflammatory processes in arthritis, oncology to cause a "cryoimmunology" effect to deal with various types of cancer (liver, lung, prostate and other organs), and in sports medicine to reduce pain in damaged muscles or ligaments. Some cryotherapeutic procedures can be used at home, for example, non-prescription wart removal devices, such as Freeze Spray.

In dermatology the current delivery methods of cryogenic liquid for skin treatment are: use of a cotton swab or spray gun and a contact cryoprobe cooled with liquid nitrogen, nitrous oxide or carbon dioxide. The method used for cryotherapy of the skin is designed to apply liquid nitrogen for significant period of time on the skin. Usually, parts of the skin surface to be treated are exposed to cryogenic liquid action for a period of time from tenths to several tens of seconds or more, depending on the desired treatment effect, which ensures rapid cooling of the skin surface and cryogenic treatment.

Another cryogenic treatment method involves using a cold source device in which cryogenic liquid is stored at a low temperature and when a cold source is activated by a dermatologist or a specialist, cryogenic liquid is displaced under pressure and applied to the skin surface to provide treatment. Such cryotherapy devices do not allow application of cryogenic liquid safely, easily and efficiently to sensitive treatment areas, such as eyelids, for example. They are also limited to small treatment sites, which limits the treatment area. Requirement for a separate source of cold limits mobility, autonomy and portability of such devices.

There is requirement for a lightweight, autonomous, user-friendly, versatile, safe, portable and low-pressure cryogenic applicator for more efficient and safe use of cryogenic liquid on the skin while minimizing losses of cryogenic liquid from evaporation during storage and use.

III. SUMMARY OF INVENTION

The invention in at least one embodiment includes a cryogenic applicator having a vessel for liquid nitrogen having at least one wall, a top, and a bottom, a vacuum casing having at least one wall, a top, and a bottom, and housing said vessel for liquid nitrogen and defining a vacuum cavity between an inner surface of said vacuum casing and an exterior surface of said vessel for liquid nitrogen, a neck extending from the top of the vessel for liquid nitrogen and through the top of said vacuum casing, the neck communicates with the vessel for liquid nitrogen, at least one capillary having an inlet disposed near the base of the vessel for liquid nitrogen and extending through the base of the vessel for liquid nitrogen and through a bottom space of the vacuum cavity formed by a bottom of the vacuum casing, a conduit extending from the bottom of the vacuum casing, said conduit housing and guiding the at least one feeding capillary, and a roller mechanism, connected to the conduit via slide bearings, wherein an outlet of the at least one capillary is housed within said roller mechanism.

The invention in an embodiment further to any previous embodiment includes a vacuum valve located on the outside of said vacuum casing and communicating with the vacuum cavity.

The invention in an embodiment further to any previous embodiment includes a control valve located at the end of said neck communicating with said vessel for liquid nitrogen.

The invention in an embodiment further to any previous embodiment includes the at least one capillary being any one of a forming capillary, a feeding capillary, or a thermostatic capillary.

The invention in an embodiment further to any previous embodiment includes the vacuum casing having an upper part having a top, a midsection part having the at least one wall, and a bottom part having the bottom. In a further embodiment, the upper part and midsection part of the vacuum casing are fixed to each other hermetically and vacuum-tightly by one or more of the following methods: welding, soldering or gluing. The midsection part and the bottom part of the vacuum casing are fixed to each other hermetically and vacuum-tightly by one or more of the following methods: welding, soldering or gluing.

The invention in an embodiment further to any previous embodiment includes an external surface of the vacuum casing having ridges.

The invention in an embodiment further to any previous embodiment includes the roller mechanism including an evaporation chamber, said evaporation chamber including the outlet of said at least one capillary, a roller retainer having a gap at least with one slide bearing, and a removable hollow roller that encases the evaporation chamber with radial holes held in place by said slide bearing and said roller retainer.

The invention in an embodiment further to any previous embodiment includes the evaporation chamber having radial holes that enable the flow of liquid nitrogen from the outlet of the forming capillary inside the evaporation chamber to a surface of the removable roller.

The invention in an embodiment further to any previous embodiment includes the roller including a porous biocompatible material. Further to this embodiment, the roller contains one or more of titanium, titanium alloy, nickel, nickel alloy, stainless steel, a biocompatible plastic compound, such as of PTFE and PTFE-based composites, or a polyimide.

The invention in an embodiment further to any previous embodiment includes a hydrogen absorber housed in a chamber having a mesh floor and disposed on the exterior of said vacuum casing and communicating with the vacuum cavity.

The invention in an embodiment further to any previous embodiment includes a cryo-adsorbent housed in a chamber having a mesh floor and located on the interior bottom of the vessel for liquid nitrogen and communicating with the vacuum cavity.

The invention in an embodiment further to any previous embodiment includes a filter located above the bottom of the liquid nitrogen vessel surrounding an inlet of the at least one capillary. Further to this embodiment, the filter includes a sintered material from metal beads including any of silver, titanium, nickel or stainless steel.

The invention in an embodiment further to any previous embodiment includes the at least one capillary extending upwards from the inlet above the bottom of the vessel for liquid nitrogen to form a U-bend near the top of the vessel and extending downward to the bottom of the vessel.

The invention in an embodiment further to any previous embodiment includes a lower end of the conduit being tilted at an angle between 45±15 degrees in relation to a longitudinal axis of the cryogenic applicator.

An alternative embodiment of the present invention includes an applicator system comprising any of the above embodiments and a stand and base. Further to this embodiment, the stand and base include a socket and a support funnel. A further embodiment of the present invention includes an applicator system including a measuring funnel for filling the vessel with liquid nitrogen through the neck.

The invention described in an alternative embodiment includes a cryogenic applicator having a vessel for liquid nitrogen having walls, a top, and a bottom; a vacuum casing having a top part, a midsection part and a bottom part, and said vacuum casing housing said vessel for liquid nitrogen and defining a vacuum cavity between an inner surface of said vacuum casing and an exterior surface of said vessel for liquid nitrogen, said bottom part of said vacuum casing forming a vertically inverted flattened cone; a vacuum valve located on an exterior surface of the top part of said vacuum casing and communicating with the vacuum cavity between said vacuum casing and said vessel for liquid nitrogen; a neck extending upward from the top of said vessel for liquid nitrogen and in communication with said vessel for liquid nitrogen, said neck having an upper end extending beyond the exterior surface of said vacuum casing and not communicating with the vacuum cavity between said vacuum casing and said vessel for liquid nitrogen; a control valve disposed near the upper end of said neck, said control valve for pressure relief in the vessel when an operating pressure is exceeded; a gasket disposed in said control valve and tightly engaged therewith, a hollow conduit extending from the bottom part of said vacuum casing; an adapter bushing disposed at an end of said conduit opposite to the bottom part of the vacuum casing, said adapter bushing having installed therearound a stopper ring with a washer, said adapter bushing connecting said conduit and said vacuum casing to a hollow evaporation chamber, said evaporation chamber having radial through holes extending from the hollow interior of said evaporation chamber to the exterior surface of said evaporation chamber; a back slide bearing fixed to said stopper ring with a washer on said adapter bushing, comprised of a material with a low friction coefficient at cryogenic temperatures; a removable rotating roller affixed to said back slide bearing, said removable rotating roller having a hollow interior of a sufficient diameter to enclose said evaporation chamber, said removable rotating roller held in place on said back slide bearing by a front slide bearing fixed to an opposite end of said roller by a roller retainer, said roller retainer limiting longitudinal movement of the roller to a pre-determined gap between the front slide bearing and the retainer and serving to reduce the heat input to a distal end of the evaporation chamber; a feeding capillary having an inlet disposed near the bottom of the vessel for liquid nitrogen and extending through and beyond the bottom of said vessel for liquid nitrogen and the bottom part of the vacuum casing and the conduit, the outlet of said feeding capillary terminating inside the hollow interior of said evaporation chamber; a forming capillary encased within said feeding capillary and having a length equal to or substantially similar to said feeding capillary; a thermostatic capillary encasing a length of the part of said feeding capillary housed within said vessel for liquid nitrogen; said feeding capillary, said forming capillary, and said thermostatic capillary having the shape of an inverted U beginning near the bottom of the vessel for liquid nitrogen, extending upwards towards the top of said vessel for liquid nitrogen, bending near the top of the vessel for liquid nitrogen, and returning downward to the bottom of the vessel for liquid nitrogen; a filter into which the inlet of said feeding capillary and forming capillary is disposed, said filter located near the bottom of said vessel for liquid nitrogen, a cryo-adsorbent disposed on the bottom of the vessel for liquid nitrogen housed in a chamber with a mesh floor, said cryo-adsorbent communicates with the vacuum cavity between said vacuum casing and said vessel for liquid nitrogen; a hydrogen absorber disposed on the exterior surface of said vacuum casing, housed in a chamber with a mesh bottom, said hydrogen absorber in communication with the vacuum cavity between said vacuum casing and said vessel for liquid nitrogen, and a stand with base including a socket and a support funnel onto which the cryogenic applicator is placed and rests.

In an alternative embodiment to those listed above, the invention in at least one embodiment includes a cryogenic applicator, having a vessel for liquid nitrogen, hermetically connected to a vacuum casing and installed inside the vacuum casing, a conduit terminating in an adapter busing and an evaporation chamber, a replaceable roller made of a biocompatible porous material, the evaporation chamber and roller being connected to the vessel for liquid nitrogen through the feeding capillary, the outlet of which is installed inside the roller and in communicates with the outer surface of the roller through the porous material of the roller.

The invention in an alternative embodiment includes a method of cryogenic skin treatment using a cryogenic applicator, including filling liquid nitrogen into the vessel for liquid nitrogen through a neck disposed near a top part of the vessel for liquid nitrogen, sealing the vessel for liquid nitrogen by blocking the neck to create a positive pressure within the vessel for liquid nitrogen, and applying a roller mechanism of the cryogenic applicator to the skin surface to be treated and dispensing liquid nitrogen onto the skin surface by rolling over the skin surface with said roller mechanism.

Given the following enabling description of the drawings, the apparatus should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements. The use of cross-hatching and shading within the drawings is not intended as limiting the type of materials that may be used to manufacture the invention.

FIG. 1 illustrates a longitudinal cross section of the cryogenic applicator according to at least one embodiment of the invention.

FIG. 3 illustrates a longitudinal cross section of the vessel for liquid nitrogen and a vacuum casing according to at least one embodiment of the invention.

V. DETAILED DESCRIPTION OF INVENTION

The present invention relates to a cryogenic applicator intended to apply a cryogenic fluid to skin surfaces for various medical and cosmetic skin care procedures and methods of use thereof. Although the following discussion is directed to using liquid nitrogen, it is understood that any appropriate cryogenic fluid, for example carbon dioxide, nitrous oxide, or dimethyl ether, may be used with the applicator.

In at least one embodiment, a portable, cryogenic applicator supplies liquid nitrogen, held in a vessel for liquid nitrogen, to an outer surface of a rotating roller made of a biocompatible porous material by supplying liquid nitrogen through a feeding capillary to an evaporation chamber and then on interior cylindrical surface of the roller. The cryogenic applicator in operation condition provides cryogenic treatment to skin surface and does not require an additional power source.

Figure 2A:
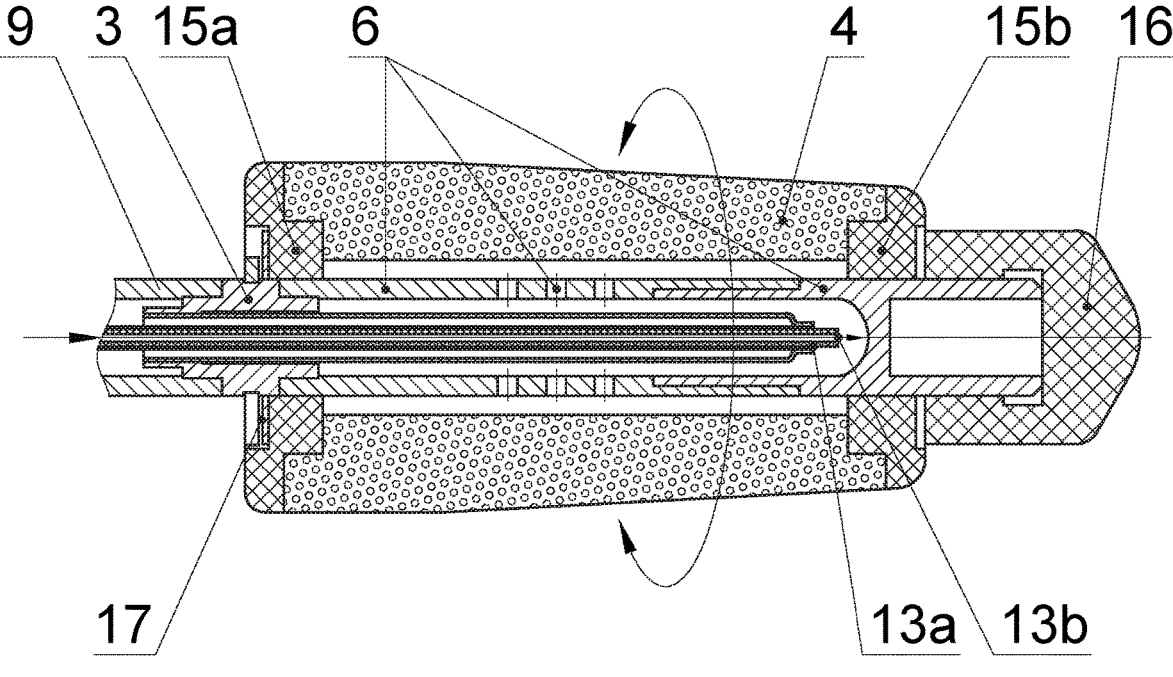
FIG. 2a and FIG. 2b illustrate a longitudinal cross section of the adapter bushing, an evaporation chamber and a roller of the cryogenic applicator according to at least one embodiment of the invention.
Figure 2B:
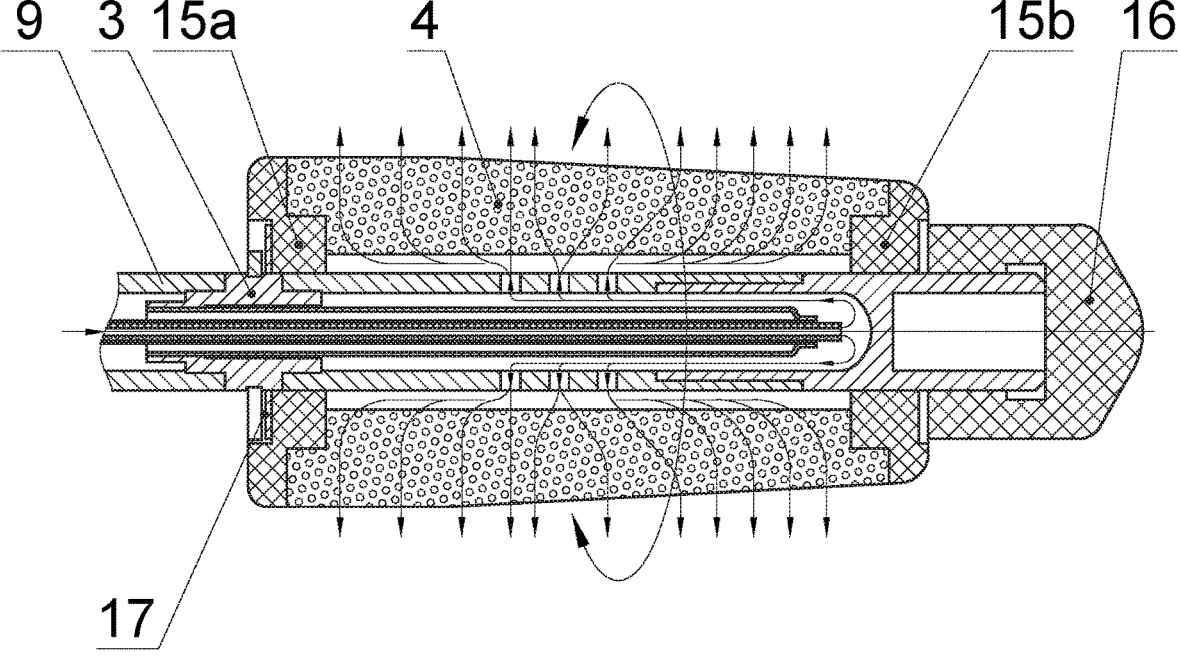

FIG. 1 illustrates an example of an apparatus according to at least one embodiment of the present invention. The apparatus as illustrated in FIG. 1 includes a vessel for liquid nitrogen 1 tightly connected with the vacuum casing and placed inside the vacuum casing 2. Conduit 9 connects to and extends from the bottom of the vacuum casing 2. The conduit 9 is connected to the evaporation chamber 6 by means of adapter bushing 3, as shown in FIGS. 2a and 2b. The rotating roller 4 on back slide bearing 15a and front slide bearing 15b is mounted on the evaporation chamber 6 and fixed to the latter by the roller retainer 16. In at least one embodiment, the rotating roller 4 is replaceable. Both the vessel for liquid nitrogen 1 and the vacuum casing 2 have a top, a bottom, and at least one wall, which is illustrated to be cylindrical.

Between the vacuum casing 2, which has an internal surface defined by the top, the bottom and the at least one cylindrical wall, and the vessel for liquid nitrogen 1, which has an external surface, there is a vacuum cavity 8, which serves to minimize external heat flow penetration to the vessel for liquid nitrogen 1, resulting in reduction of losses of liquid nitrogen, and to maintain the external surface of the vacuum casing 2 at an ambient temperature. Vacuum insulation from low temperatures created inside the vessel 1 by liquid nitrogen, which has a boiling point of minus 196° C., provides certain safety level for the user, since most elements (except for the cold rotating roller 4) can be safely touched during the procedure without use of special insulating gloves.

The vacuum casing 2 is equipped with a vacuum and safety valve 10. During cryogenic applicator production, a vacuum key engages with a vacuum pump and open vacuum and safety valve 10 to create a vacuum in the vacuum cavity 8. After creation of a vacuum in the vacuum cavity 8 of at most $10^{-6}$ mm Hg, the vacuum and safety valve 10 is closed to keep a residual vacuum in the vacuum cavity 8. The vacuum and safety valve 10 also functions as a safety valve to drop overpressure in the vacuum cavity 8 in case of its depressurization. Both elements of a vacuum valve and a safety valve 10 are reusable.

In at least one embodiment, the vacuum and safety valve 10 rises and provides a pathway for gas evacuation from the vacuum cavity 8 through a plurality of spaced vents around the top of the vacuum and safety valve 10. The vacuum casing 2 includes external ribs, as shown in the FIG. 1. The external ribs provide a texture surface easy for work with the cryogenic applicator. In at least one embodiment, the external ribs are embossed on the vacuum casing perpendicular to the longitudinal axis of the vacuum casing 2. Alternative embodiments feature an external surface having a roughened texture or knurling for easy handling. Alternatively, the external surface of the vacuum casing 2 may feature a grip from plastic or soft rubber-like material for comfort to the user. The vacuum casing 2 can be assembled via interference fitting, for example, a top portion, a middle or midsection section and a bottom portion having the shape of a vertically inverted flattened cone.

The vessel 1 is equipped with a control valve 14 that also operates as a safety valve. The control and safety valve 14 is installed on the top end of a neck 18 of the vessel 1 and tightly closes the neck 18 with gasket 19. The control and safety valve 14 communicates with the vessel for liquid nitrogen 1 via the neck 18 and serves to create operation pressure into the vessel 1 and to discharge excess gas pressure within the vessel 1 into the atmosphere.

Inside the vessel 1 there is a cryo-adsorbent 7 stored within a housing projecting upward from the floor of the vessel 1 and open to the vacuum cavity 8 through metal mesh 22a, as shown in FIG. 3. The cryo-adsorbent 7 cools down to the liquid nitrogen temperature after filling the vessel 1 with liquid nitrogen. The cryo-adsorbent 7 is activated by low temperature to adsorb residual gases in the vacuum cavity 8, serving to improve vacuum insulation between the vessel 1 and the vacuum casing 2.

On the outer surface of the vacuum casing 2 there is a hydrogen absorber 20. The hydrogen absorber 20 is placed within a housing open to the vacuum cavity 8 through metal mesh 22b, as shown in FIG. 3, and serves to absorb hydrogen which with time escapes from the surfaces inside of the vacuum cavity 8 and deteriorates vacuum insulation. The hydrogen absorber 20 enables prolonged vacuum insulation in the vacuum cavity 8 without additional maintenance. The hydrogen absorber 20 has a temperature equal to the temperature of external surface of the vacuum casing 2 and works regardless of the presence or absence of liquid nitrogen in the vessel 1, thus preventing loss of vacuum in the vacuum cavity 8 due to at least hydrogen escaped from surfaces in the vacuum cavity 8.

The cryo-adsorbent 7 and the hydrogen absorber 20 are each secured within their respective housings that are closed off at the bottom side with a metal mesh, to allow communication between the respective materials of the cryo-adsorbent 7 and the hydrogen absorber 20 and the vacuum cavity 8.

In a specific embodiment, the conduit 9 is tilted at an angle of 45±15° to the longitudinal axis of the vessel 1, enabling the user to work with the device both in vertical and in horizontal positions relative to the surface to be treated.

The rotating roller 4 is made of a porous material and has internal opened and interconnecting pores to enable easy pass of liquid nitrogen therethrough. The porous material of the rotating roller 4 can be any biocompatible material. For example, for a durable and reusable roller, biocompatible metals can be used. Examples of biocompatible metals include, but are not limited to, titanium, titanium-base alloy, nickel, nickel-base alloy, or stainless steel. For use over a longer span of time, the biocompatible metal rotating roller can be used in conjunction with a disposable tubular bandage for hygiene purposes, which can be subsequently discarded and replaced with each use of the applicator. The rotating roller can alternatively be composed of a biocompatible plastic as an inexpensive alternative to metal, for shorter-term or single-use application. Biocompatible plastic options for the rolling roller 4 include, but are not limited to, PTFE and PTFE-based composites, polyimides such as KAPTON®, polyvinyl chloride (PVC), polyethylene, polycarbonate, polyether ether ketone (PEEK), polypropylene, polysulfone, or polyurethane. The rotating roller 4 can be of any external shape to facilitate effective delivery of liquid nitrogen onto the targeted skin surface. For example, the rotating roller 4 may be in a cylindrical shape, or in a truncated conical shape.

Capillaries 5a, 5b and a thermo-static capillary 5c are installed inside the vessel 1, and capillaries 5a and 5b travel through the conduit 9 and end inside an evaporation chamber 6 within the rotating roller 4. Feeding capillary 5a inside the vessel 1 has an inlet 12a inside a filter 21, as shown in FIG. 3, which is in communication with the vessel 1. The inlet 12b of forming capillary 5b is disposed slightly upstream of the inlet 12a of feeding capillary 5a. In at least one embodiment, the filter 21 is a sintered material from metal balls or thin metal mesh including, but not limited to, any of silver, titanium, nickel or stainless steel, capable of holding condensate water and possible pollutions out of the cryogenic liquid prior to passing into the feeding capillary 5a.

The entire length or part thereof inside of the feeding capillary 5a encases the forming capillary 5b. In at least one embodiment, the feeding capillary 5a is a thin and durable capillary pipe formed of a material with low thermal conductivity. For example, the feeding capillary 5a may be composed of any appropriate plastic or metal material, among others, stainless steel. The forming capillary 5b is inserted into the feeding capillary 5a along its entire length, and, in at least one embodiment, the forming capillary 5b has a smooth inner surface to create a laminar flow of liquid nitrogen. The forming capillary 5b can be composed of, for example, PTFE or a PTFE-based composite. The thermo-static capillary 5c encases the feeding capillary 5a along its entire length within the vessel for liquid nitrogen 1. In at least one embodiment, the thermostatic capillary 5c includes material with high thermal conductivity, for example, a metal such as copper or silver. The thermostatic capillary 5c serves to maintain temperature of liquid nitrogen inside the feeding capillary 5a in case of changing liquid nitrogen level in the cryogenic vessel 1. This is helpful to prevent or at least reduce changing the liquid nitrogen into gaseous state within the feeding capillary 5b at a U-bend 11 when the level of liquid nitrogen within the vessel 1 is reduced below U-bend during work with the cryogenic applicator.

In at least one embodiment of the present invention as illustrated in FIG. 3, the inlet 12a of the feeding capillary 5a is cut at an angle to its axis to prevent blocking and facilitate supply of the liquid nitrogen from the filter 21 into the capillaries 5a, 5b.

The shape of the capillaries 5a, 5b, 5c within the vessel 1 forms a U-bend 11, starting from the filter 21 at the base of the vessel 1 and forming a top bend close to the neck 18 at the top of the vessel 1. Such shape of the capillaries 5a, 5b, 5c serves to prevent or at least reduce spontaneous discharge of the liquid nitrogen through the capillary during filling or refilling of the device with liquid nitrogen, or before operation when the neck 18 of the device is open. After filling or refilling the cryogenic applicator, to supply the liquid nitrogen through the capillaries 5a, 5b to the roller 4, it is necessary to seal the neck 18 with the control valve 14 and the gasket 19. When the neck 18 is sealed after loading the liquid nitrogen into the vessel 1, slight overpressure within the cryogenic vessel 1 which occurs when the liquid nitrogen evaporates due to heat input from outside (volume of the evaporated part of the liquid nitrogen increases significantly when passing into the gaseous state, which creates overpressure), causes forced supply of the liquid nitrogen through the capillaries 5a, 5b, to the roller 4.

The control and safety valve 14 serves simultaneously to discharge overpressure in the vessel 1 into the surrounding atmosphere. If necessary, the control valve 14 may be adjusted manually to set work pressure inside the vessel 1. As shown in FIG. 1 the control and safety valve 14 also includes a sealing gasket 19 to prevent pressure drop and loss of liquid nitrogen from the vessel 1 after its loading. The sealing gasket 19 can be of any appropriate dimension to seal the control and safety valve 14, for example, a conical shape.

FIGS. 1, 2a, and 2b illustrate an example of an apparatus according to at least one embodiment. There is the rotating roller 4 at the end of the conduit 9. The conduit 9 is a hollow tube and includes in its interior capillaries 5a, 5b and is an extension of the vacuum casing 2 in its lower part. Adapter bushing 3 is installed at the end of the conduit 9 opposite to the end extending from the bottom portion of the vacuum casing 2. The back slide bearing 15a is affixed to a stopper ring with washer 17 that is installed on the adapter bushing 3. At the end of the adapter bushing 3 opposite to the end on which the conduit 9 is installed, an evaporation chamber 6 is installed. The evaporation chamber 6 has radial through holes disposed along the length. The through holes extend from the hollow interior of the evaporation chamber 6 to its exterior surface. The rotating roller 4 is mounted on back slide bearing 15a and front slide bearing 15b on the evaporation chamber 6 and secured with the roller retainer 16. In at least one embodiment, the slide bearings 15a, 15b are made of a material with low coefficient of friction at cryogenic temperatures to facilitate rotating of the roller 4. For example, the back and front slide bearings 15a,15b can be made of PTFE or a PTFE-based composite material.

The feeding and forming capillaries 5a, 5b travel through the conduit 9 from the bottom of the vessel 1, through the adapter bushing 3, and terminate at their respective outlets 13a, 13b. The outlets 13a, 13b terminate in the hollow interior of the evaporation chamber 6 and liquid nitrogen from outlet 13b of the forming capillary is released into the evaporation chamber 6 under pressure during operation of the cryogenic applicator. The radial through holes of the evaporation chamber 6 allow for transport of the liquid nitrogen from the evaporation chamber 6 to the interior surface of the roller 4 as illustrated, for example, in FIG. 2b. The porous material of which the roller 4 is made from allows for liquid nitrogen to pass through the open pores to the exterior surface of the roller 4, which exterior surface contacts the skin surface during treatment. The slide bearings 15a, 15b provide easy rotation of the roller 4, which is held in place on the adapter bushing 3 and the evaporation chamber 6 by the retainer 16.

At least one of the functions of the roller retainer 16 is to limit the longitudinal movement of the roller 4 to a predetermined gap between the front slide bearing 15b and the retainer 16. At least another function of the retainer 16 is to reduce heat flow to the distal end of the evaporation chamber 6, which minimizes overhead loss of the liquid nitrogen in the evaporation chamber 6 and the roller 4. For this purpose, the retainer 16 can be made of a material with low thermal conductivity, for example, from a composite material based on PTFE.

Pressure within the cryogenic vessel 1 increases due to evaporation of the liquid cryogen caused by heat input from outside. The range of working pressure in the device, after primary filling with liquid nitrogen is complete and cooling of the internal parts, depends upon the level of external heat penetration and the primary setting of the control valve 14, and in at least one embodiment is in the range of 0.01-0.5 bar. At a pressure greater than or equal to 0.1 bar, liquid nitrogen is supplied through the inlet 12a of the feeding capillary 5a, located inside the filter 21 at the bottom of the vessel 1. The liquid nitrogen under pressure continues to flow through the capillaries 5a, 5b to the outlets 13a, 13b into the interior of the evaporation chamber 6. The liquid nitrogen transfers through the radial holes of the evaporation chamber 6 and through the porous body of the roller 4 to the outer working surface of the roller 4, cooling it down to a cryogenic temperature, and has cryo-therapeutic effect when rolled on the skin surface.

FIG. 3 illustrates the U-bend 11 of the capillaries 5a, 5b, 5c within the vessel 1 near the top of the vessel 1. FIG. 3 also illustrates the temperature zones within the vessel 1, illustrating that the thermo-static capillary 5c keeps safe liquid nitrogen inside the forming capillary 5b from changing its temperature throughout the length of the capillary that is housed inside the cryogenic vessel 1. Additionally, the thermo-static capillary 5c prevents gas phase creation in liquid nitrogen flowing into a higher temperature zone T2 as compared to when it enters the forming capillary 5b at the bottom of the vessel in lower temperature zone T1 (temperatures T3 and T4 in forming capillary 5b are substantially the same as temperature zone T1). The temperature in the T2 zone is higher than the temperature in the T1 zone, because T2 characterizes a space that is not filled with liquid nitrogen, and because it is closer to such heat sources from the outside, as the neck 18 and the control valve 14. This part of vessel 1 is cooled in the last place after the completion of the filling of vessel 1 and is first heated when liquid nitrogen in vessel 1 ends or vessel 1 opens to refilling. As such, it is useful to stabilize the temperature such as by using a thermo-static capillary 5c to ensure liquid nitrogen in the forming capillary 5b does not change temperature when traveling through U-bend from temperature zone T1 to temperature zone T2.

FIG. 3 additionally illustrates an embodiment of the invention having cryo-adsorbent 7 and hydrogen absorber 20 in their respective housings closed on one side with metal mesh 22a and 22b.

Figure 4:
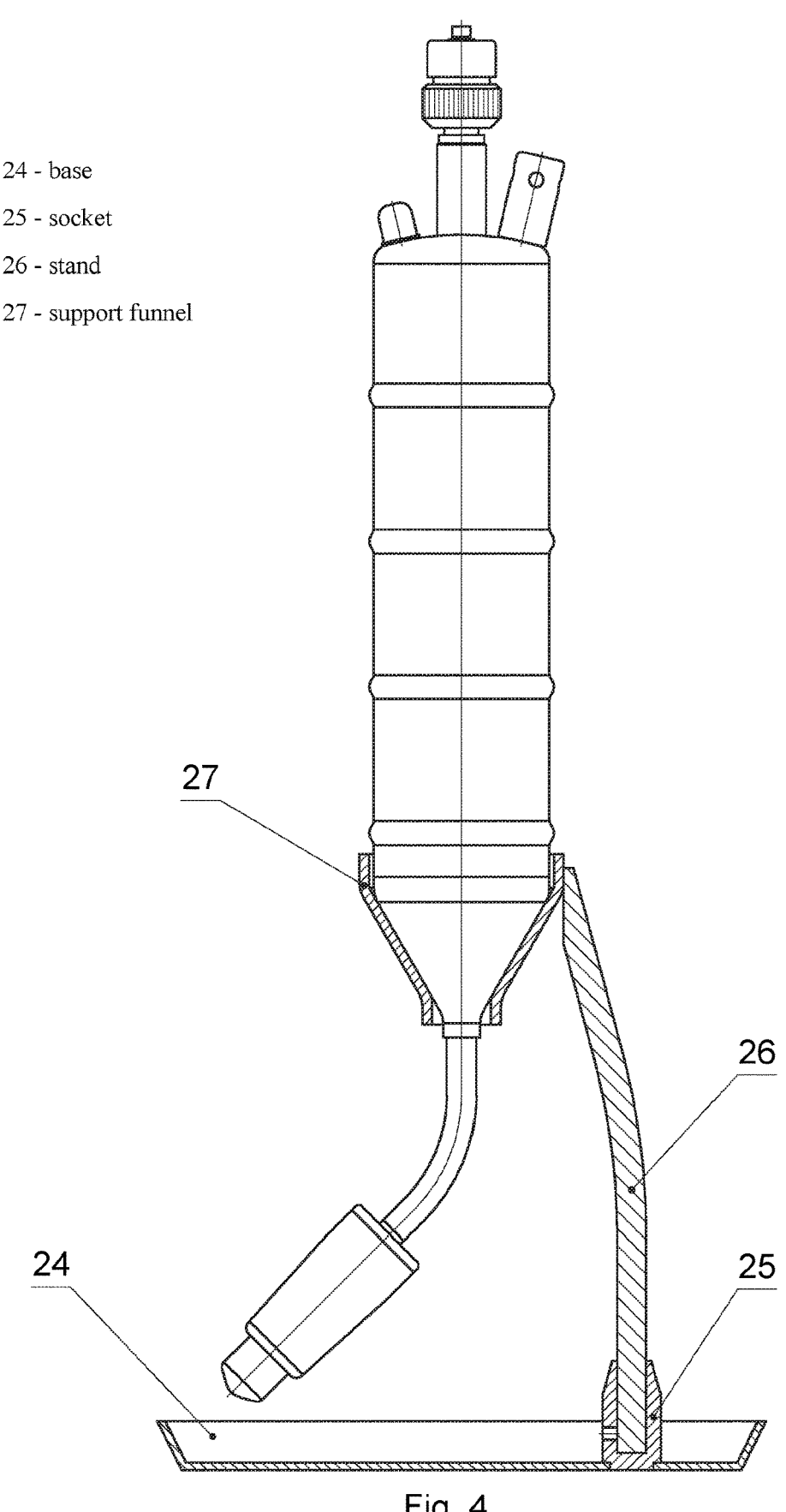
FIG. 4 illustrates a side view of the cryogenic applicator and a stand and base according to at least one embodiment of the invention.

FIG. 4 illustrates an embodiment of the invention in which the cryogenic applicator is placed vertically in the support funnel 27 on the stand 26. The stand 26 has a base 24 onto which a socket 25 is installed. The support funnel 27 has a suitable size, shape and longitudinal slit for quick and stable placement and support of a cryogenic applicator by installing and fixing on the outer surface.

The embodiments described above may be combined in a variety of ways with each other. Furthermore, the steps and number of the various steps discussed may be adjusted. It should be noted that the present invention may, however, be embodied in many different forms and should not be construed as limited to the embodiments set forth herein; rather, the embodiments set forth herein are provided so that the disclosure will be thorough and complete, and will fully convey the scope of the invention to those skilled in the art. The accompanying drawings illustrate exemplary embodiments of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to explain the principles of the invention and the practical application, and to enable others of ordinary skill in the art to understand the invention for various embodiments with various modifications as are suited to the particular use contemplated.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

As used "any of" or "any one of" when used with a list of items are meant to identify items that may be used individually or in some combination such that when not used are not present.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

VI. INDUSTRIAL APPLICABILITY

The present invention relates to medical equipment, namely to cryogenic applicators intended to apply a cryogenic fluid, for example liquid nitrogen, to skin surfaces for various medical and cosmetic skin care procedures, and methods of use thereof.

REFERENCE NUMBERS

1. Vessel for liquid nitrogen
2. Vacuum casing
3. Adapter bushing
4. Roller
5a. Feeding capillary
5b. Forming capillary
5c. Thermo-static capillary
6. Evaporation chamber with radial holes
7. Cryo-adsorbent
8. Vacuum cavity
9. Conduit
10. Vacuum and safety valve
11. U-bend
12a. Inlet of the feeding capillary
12b. Inlet of the forming capillary
13a. Outlet of the feeding capillary
13b. Outlet of the forming capillary
14. Control and safety valve
15a. Back slide bearing
15b. Front slide bearing
16. Roller retainer
17. Stopper ring with washer
18. Neck
19. Gasket
20. Hydrogen absorber
21. Filter
22a. Metal mesh
22b. Metal mesh
23. Liquid nitrogen level
24. Base
25. Socket
26. Stand
27. Support funnel
T1. Temperature of liquid nitrogen
T2. Temperature above liquid nitrogen level
T3. and T4. Temperature in forming capillary 5b.
What is claimed is:

1. A cryogenic applicator, comprising:
a vessel for liquid nitrogen having at least one wall, a top, and a bottom,
a vacuum casing having at least one wall, a top, and a bottom, and housing said vessel for liquid nitrogen and defining a vacuum cavity between an inner surface of said vacuum casing and an exterior surface of said vessel for liquid nitrogen,
a neck extending from the top of said vessel for liquid nitrogen and through said top of said vacuum casing, said neck communicates with said vessel for liquid nitrogen,
a forming capillary which is encased by a feeding capillary along the entire length of the forming capillary within the vessel,
a thermostatic capillary which encases the feeding capillary along the entire length of the feeding capillary within the vessel,
a conduit extending from the bottom of the vacuum casing, and a roller mechanism connected to said conduit via slide bearings, wherein the outlets of the feeding capillary and the forming capillary terminate in an evaporation chamber housed within said roller mechanism, and
a filter located above the bottom of the vessel for liquid nitrogen, surrounding an inlet of the feeding capillary, wherein each of the feeding capillary, the forming capillary, and the thermostatic capillary extend upward from the filter and all together form a U-bend near the top of the vessel and each extend to the bottom of the vessel.

2. The cryogenic applicator of claim 1, further comprising a vacuum valve located outside of said vacuum casing and communicating with the vacuum cavity.

3. The cryogenic applicator of claim 1, further comprising a control valve located at the end of said neck communicating with said vessel for liquid nitrogen.

4. The cryogenic applicator of claim 1, wherein said vacuum casing has an upper part having a top, a midsection part having the at least one wall, and a bottom part having the bottom.

5. The cryogenic applicator of claim 4, wherein the upper part and the midsection part of the vacuum casing are fixed to each other hermetically and vacuum-tightly by one or more of welding, soldering or gluing; and the midsection part and the bottom part of the vacuum casing are fixed to each other hermetically and vacuum-tightly by one or more of welding, soldering or gluing.

6. The cryogenic applicator of claim 1, wherein said roller mechanism further comprises:
a roller retainer having a gap at least with one slide bearing, and
a porous roller that encases the evaporation chamber,
wherein said evaporation chamber has radial holes extending from an interior surface of the evaporation chamber to an exterior surface of the evaporation chamber and configured to allow transport of liquid nitrogen from an outlet of the forming capillary to an interior surface of the removable porous roller held in place by said at least one slide bearing and said roller retainer,
wherein the porous roller comprises a porous biocompatible material to enable liquid nitrogen to pass through pores of the porous roller from the interior surface of the porous roller to an exterior surface of the removable porous roller.

7. The cryogenic applicator of claim 6, wherein the porous roller comprises any one of titanium, titanium-base alloy, or nickel, nickel-base alloy.

8. The cryogenic applicator of claim 6, wherein the porous roller comprises PTFE or a PTFE-based composite.

9. The cryogenic applicator of claim 1, further comprising a hydrogen absorber housed in a chamber having a mesh floor and disposed on the exterior of said vacuum casing and communicating with the vacuum cavity.

10. The cryogenic applicator of claim 1, further comprising a cryo-adsorber housed in a chamber having a mesh floor and located on the interior bottom of the vessel for liquid nitrogen and communicating with the vacuum cavity.

11. The cryogenic applicator of claim 1, wherein said filter comprises a sintered material from metal beads including any of silver, titanium, nickel or stainless steel.

12. The cryogenic applicator of claim 1, wherein a lower end of said conduit is tilted at an angle 45±15 degrees in relation to a longitudinal axis of the cryogenic applicator.

13. An applicator system comprising:

the cryogenic applicator of claim 1;

a stand and base, wherein the stand and base comprise a socket and a support funnel; and a measuring funnel for filling the vessel with liquid nitrogen through the neck.

14. A method of cryogenic skin treatment using a cryogenic applicator of claim 1, comprising:

filling liquid nitrogen into the vessel through a neck disposed near a top part of the vessel for liquid nitrogen;

sealing the vessel for liquid nitrogen by blocking the neck to create a positive pressure within the vessel for liquid nitrogen; and applying the roller mechanism to the skin surface to be treated and dispensing liquid nitrogen onto the skin surface by rolling over the skin surface with said roller mechanism.

15. The cryogenic applicator of claim 1, wherein a longitudinal axis of the roller mechanism is parallel to a longitudinal axis of the feeding capillary and the forming capillary within the evaporation chamber.

16. A cryogenic applicator, comprising:

a vessel for holding a cryogenic fluid;

a vacuum casing housing the vessel;

a forming capillary which is encased by a feeding capillary along the entire length of the forming capillary within the vessel, a thermostatic capillary which encases the feeding capillary along the entire length of the feeding capillary within the vessel;

a conduit extending from a bottom of the vacuum casing;

an evaporation chamber at the end of the conduit and in which an outlet of the the feeding capillary and an outlet of the forming capillary terminate; and a rotating roller comprising a porous biocompatible material and mounted around the evaporation chamber;

wherein the evaporation chamber has radial holes extending from an interior of the evaporation chamber to an exterior of the evaporation chamber and configured to allow transport of the cryogenic fluid from an outlet of the forming capillary through the radial holes to an inner surface of the porous biocompatible material, wherein the porous biocompatible material is configured to enable liquid nitrogen to pass through pores of the porous biocompatible material from the interior surface of the porous biocompatible material to an exterior surface of the porous biocompatible material, wherein an inlet of the feeding capillary is in a filter within the vessel and is cut at a slanted angle with respect to its longitudinal axis, and wherein each of the feeding capillary, the forming capillary, and the thermostatic capillary extend upward from the filter and all together form a U-bend near the top of the vessel and each extend to the bottom of the vessel.

17. The cryogenic applicator of claim 1, wherein:

the feeding capillary comprises a metal and is configured to supply liquid nitrogen to the roller mechanism;

the forming capillary comprises PTFE or a PTFE-based composite and is configured to create a laminar flow of liquid nitrogen that is supplied to the roller mechanism; and the thermostatic capillary comprises copper or silver and is configured to maintain a temperature of the liquid nitrogen in the feeding capillary.

18. The cryogenic applicator of claim 1, wherein an inlet of the forming capillary is recessed from an inlet of the feeding capillary within the filter.

19. The cryogenic applicator of claim 1, wherein an inlet of the feeding capillary is cut at a diagonal with respect to its longitudinal axis.

* * * * *